United States Patent [19]

Rabischong et al.

[11] 4,120,297
[45] Oct. 17, 1978

[54] ORTHOPEDIC CORSET

[75] Inventors: Pierre Rabischong, Saussan; Jean-Pierre L. Bel, Montpellier, both of France

[73] Assignee: Institut National de la Sante Et de la Recherche Medicale, Paris, France

[21] Appl. No.: 771,549

[22] Filed: Feb. 24, 1977

[30] Foreign Application Priority Data

Mar. 5, 1976 [FR] France .................................. 76 07576

[51] Int. Cl.$^2$ .............................................. A61F 5/02
[52] U.S. Cl. ................................ 128/78; 128/DIG. 20
[58] Field of Search ............... 128/78, 87 R, DIG. 20, 128/133, 134; 2/DIG. 3

[56] References Cited

U.S. PATENT DOCUMENTS

| 894,066 | 7/1908 | Scarpa | 128/78 |
|---|---|---|---|
| 1,843,527 | 2/1932 | Tubiolo | 128/87 R X |
| 1,924,016 | 8/1933 | Barrows | 128/78 |
| 2,397,709 | 4/1946 | Versoy et al. | 128/78 X |
| 2,632,178 | 3/1953 | Kennedy | 128/78 X |
| 3,292,616 | 12/1966 | Freeman | 128/78 |
| 3,871,367 | 3/1975 | Miller | 128/78 |

Primary Examiner—John D. Yasko
Attorney, Agent, or Firm—Lewis H. Eslinger

[57] ABSTRACT

Orthopedic corsets for supporting the trunk and correcting deformations of the spine, composed of a vest made of non-stretch material which envelopes the trunk, two vertical stiffening structures fixed in the center of the front and rear of said vest and an inflatable bag placed against the abdominal cavity.

11 Claims, 7 Drawing Figures

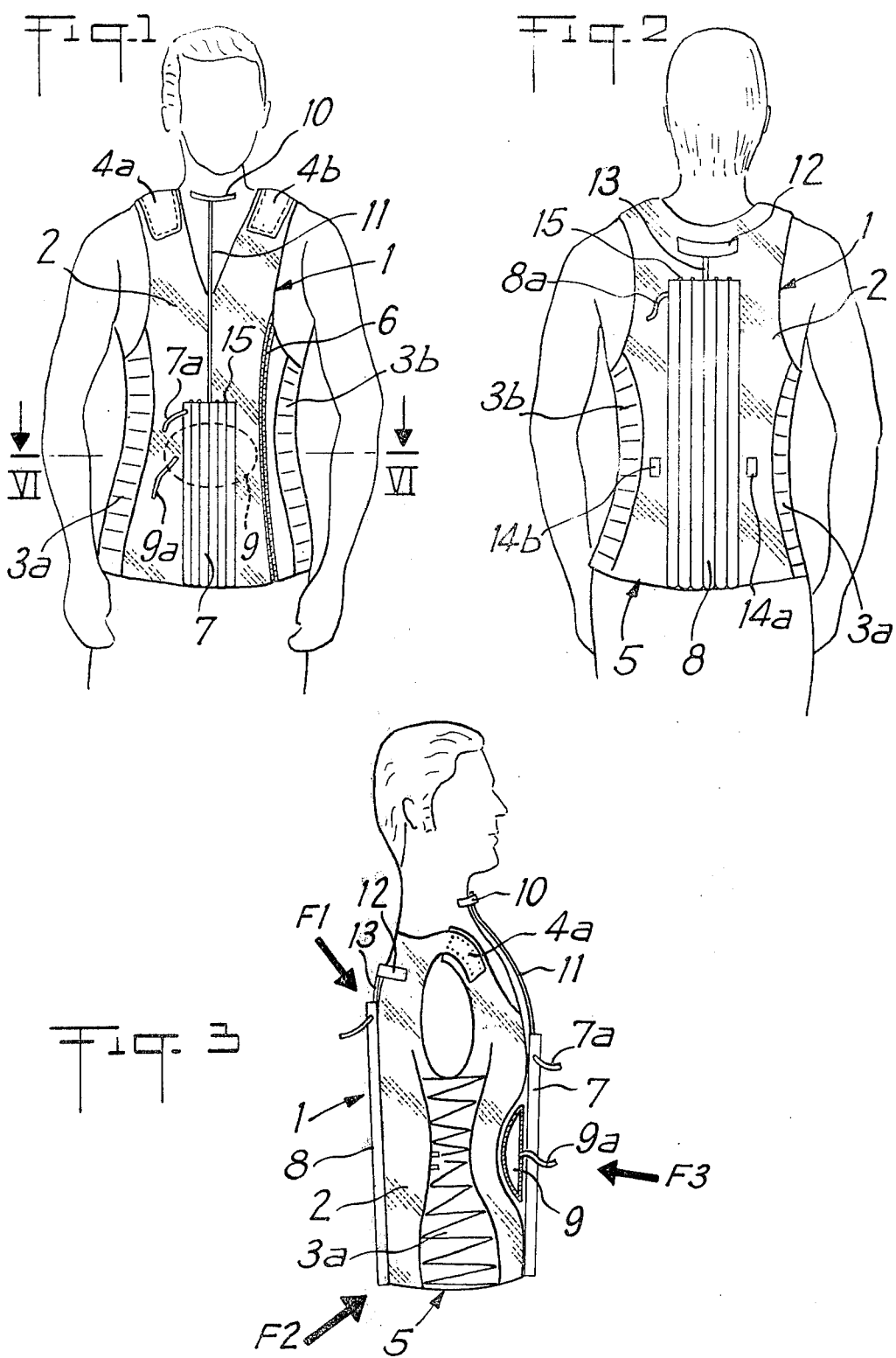

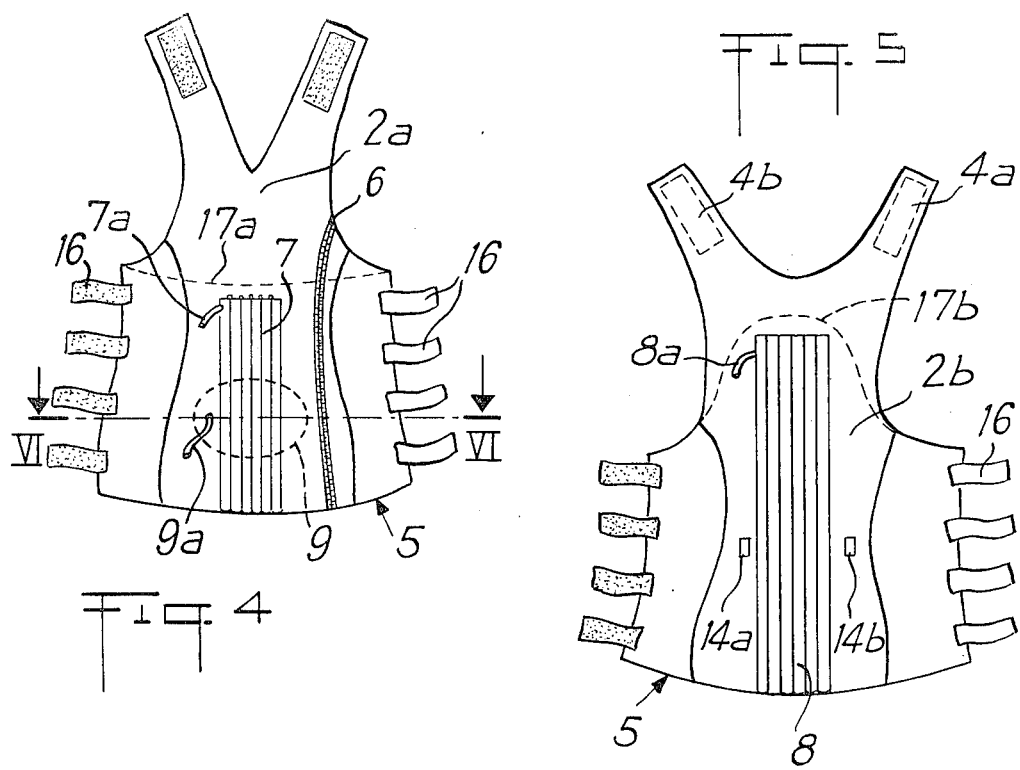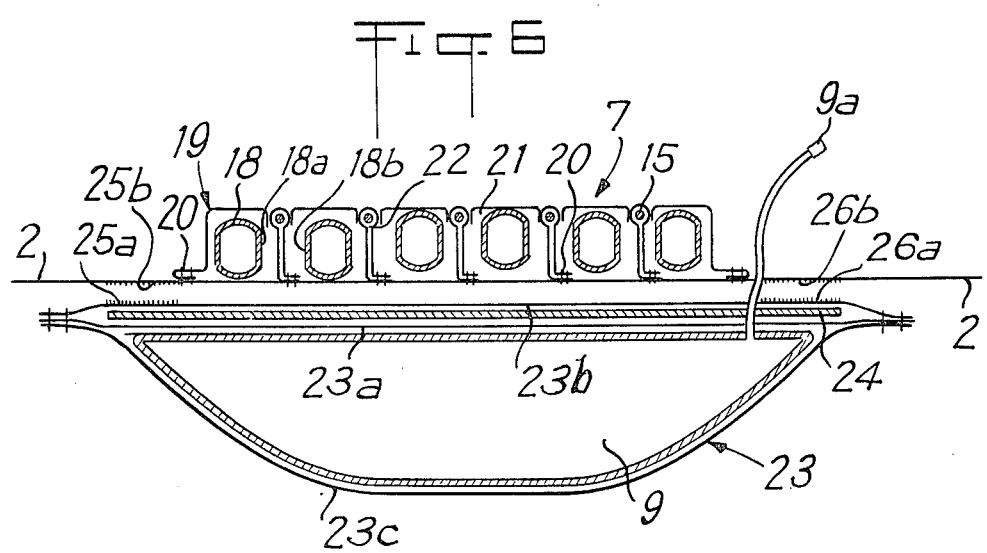

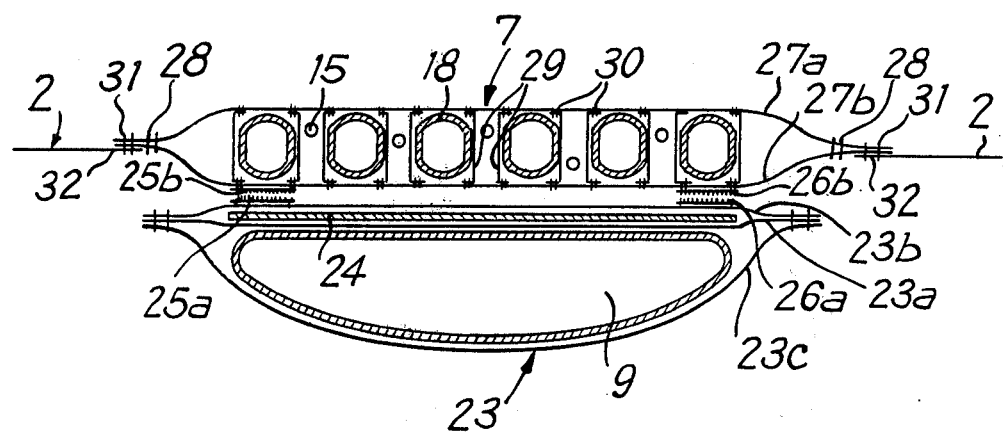

ORTHOPEDIC CORSET

The present invention relates to orthopaedic corsets for correcting the deformations or malformations of the spine.

An orthopaedic treatment of the irreducible cyphoses of the adolescent and of the anteroposterior curvatures of the dorsal or lumbar rachis, and of deformations of the rib cage, is known, which consists in reducing the cyphotic curvature by making a plastered corset on the patient in position of reduction. This corset has to be worn for an average period of three months, after which it is replaced by a corset made of rigid plastics material. A plaster corset may weigh between 5 and 50 kg depending on the child's build and it is laborious to wear.

It is an object of the present invention to produce orthopaedic corsets which enable the same results to be obtained whilst being much lighter and more pleasant to wear.

Another object of the invention is to mass produce orthopaedic corsets in ranges covering several sizes which are subsequently adjusted to the patient's body.

To this end, the invention relates to an orthopaedic corset for correcting the deformations of the spine, which comprises:

a vest made of non-stretch material which envelopes the trunk;

two stiffening structures, a front one and a rear one, each composed of a plurality of vertical inflatable tubes, which structures are fixed to said vest, the rear structure along the axis of the back and the front structure in the center of the front;

and an inflatable bag placed against the abdominal cavity under said front structure.

According to a feature of the present invention, the stiffening structures comprise, in addition:

vertical deformable sheaths arranged between the inflatable tubes;

and rigid pins placed in certain of said sheaths.

According to a further feature, the front stiffening structure extends from the sternum to the lower edge of the vest which is located approximately at the level of the pubis.

According to yet another feature, the rear stiffening structure extends from the shoulder blades to the lower edge of the vest which is located approximately at the level of the sacrum.

According to a further feature, a semi-rigid plate is preferably arranged between the abdominal bag and the front inflatable structure.

According to yet another feature of the invention, the corset may comprise a chin support and/or a nape support carried by a rigid rod which is threaded in one of the deformable sheaths of one and/or the other of the inflatable structures, this enabling the height of the supports to be adjusted.

In a preferred embodiment of the invention, each tube of the inflatable structures is enclosed in a deformable sheath formed by a band of fabric whose edges are sewn to the outside of the vest.

The present invention results in a novel orthopaedic corset for correcting the deformations or malformations of the spine and of the rib cage, particularly the antero-posterior curvature of the dorsal and lumbar rachis.

A corset according to the invention offers the following advantages:

it is light, about 500 grams, therefore not too tiring to wear;

it is well ventilated and the contact with the skin is not too unpleasant;

it may be removed for a few minutes each day to allow the patient to wash; this is obviously impossible with plaster corsets;

it replaces not only plaster corsets, but also the rigid plastics corsets which have to be worn immediately after the plaster ones.

By employing different pressures for inflating the tubes of the two structures and the abdominal bag, it is possible to vary the corrective action depending on the deformation to be corrected.

Another advantage of the orthopaedic corsets according to the invention lies in the fact that they may be industrially mass-produced in different sizes, this enabling each patient to buy a corset in his size without having to resort to a made-to-measure corset, made on himself, as in the case of plaster corsets.

In the case of the front and back of the vest being separate, it is possible to manufacture for each size several backs and several fronts comprising inflatable structures of different lengths, this enabling a back and a front of the desired size to be matched, comprising structures whose length is adapted to each particular malformation.

Orthopaedic clothing enabling paralytics to stand up is already known which comprises an article of clothing made of fabric and inflatable structures which enable it to be vertically stiffened.

The orthopadeic corsets according to the invention constitute novel applications of these inflatable structures whose function is no longer to stiffen the article of clothing vertically, but also to exert horizontal forces on the spine and to serve as support for the abdominal bag in order to straighten the spine.

The rigid rods inserted in the intermediate sheaths between the inflatable tubes improve the transverse stiffness of the corset so that said latter straightens the spine and maintains it in this position. These rods are gripped by the tubes when the tubes are inflated and it is very easy to remove them from their sheath after having deflated the tubes. They may be engaged in their housing after the vest has been put on, so that it is a simple matter to remove the vest and put it on again.

The invention will be more readily understood on reading the following description with reference to the accompaning drawings, in which:

FIGS. 1, 2 and 3 are front, back and side views respectively of a patient wearing an orthopaedic corset according to the invention.

FIGS. 4 and 5 are views of the front and back of a corset according to the invention, in two parts.

FIG. 6 is a horizontal section through VI-VI of FIGS. 1 and 4.

FIG. 7 is a horizontal section through a variant embodiment, along VI-VI.

Referring now to the drawings, FIGS. 1, 2 and 3 show a first embodiment of an orthopaedic corset 1 for correcting the malformations of the spine or the rib cage, particularly a corset for reducing the cyphoses and lordoses of an adolescent.

The corset 1 comprises a vest 2 made of fine, non-stretch fabric which is well ventilated and very resistant, which envelopes the whole trunk. In the example shown, the vest 2 also passes over the shoulders, but a vest could also be employed as a variant which does not cover the shoulders.

The vest 2 is in one piece. On the sides beneath the arm-pits, it comprises two deformable, expansible side elements whose front and rear edges are connected by laces or straps 3a and 3b, which enable the vest to be fitted closely to the chest.

The back of the vest is provided with the two adjustable tabs 4a and 4b which pass over the shoulders and overlap tabs which extend upwardly from the front of the vest. Means such as so-called touch and close fasteners or press studs enable the front and rear tabs to be fastened to one another so that the vest fits closely on the shoulders.

The lower edge 5 of the vest is located substantially at the level of the sacrum.

The vest shown in FIGS. 1, 2 and 3 further comprises closure means, for example a slide fastener 6, located on the left-hand side of the front, which makes it possible to remove and replace the vest without modifying the body adjustment.

The corset 1 further comprises two vertical inflatable structures 7 and 8. The structure 7 is fixed to the front of the vest, in the axis of the abdominal part. The structure 8 is fixed in the axis of the back. Each of these structures is composed of a plurality of inflatable, flexible tubes, which are placed side by side in parallel and fixed vertically to the back or front of the vest. Once inflated, these tubes give the vest both a vertical and transverse stiffness in order to block the movements of the pelvis. At the same time, they provide the three supports necessary to reduce the cyphotic curvature, two of these supports being along the back, one at the top of the dorsal cyphosis and the other at the level of the sacrum, blocking any possibility of forward inclination of the pelvis, and the third support being at the front at a level between those of the two rear supports, i.e. at the level of the abdomen. These supports are designated by arrows F1, F2 and F3.

In order to control the elastic deformation of structures 7 and 8, said latter comprise deformable sheaths arranged between the inflatable tubes and open at their upper end.

A rigid pin 15, for example a steel rod or a rigid, fibre-reinforced rod, e.g. carbon fibre reinforced epoxy resin, is threaded in each of said sheaths. These rods are threaded in the sheaths when the tubes are deflated and they are held in place by the tubes which grip them when they are inflated.

A corset according to the invention further comprises an inflatable abdominal bag 9 constituted by a deformable bladder placed inside the vest against the abdominal cavity.

This bag abuts against the structure 7 which serves as sternal support. It constitutes the third point of support (abdominal), holds in the viscera, enables the diaphragm to be blocked and maintains the lumbar region straight. Due to the three points of support given by the rear structure 8 and by the bag 9, any active straightening-up effort by the patient is localised on the cyphosis.

The pressurisation of the inflatable tubes and of the bag 9 is ensured by three separate mouthpieces 7a, 8a and 9a, which enables the structures and the bag to be inflated to different pressures and a balance to be obtained of the corrective action corresponding to each malformation. The pressures are then maintained for the whole period of time during which the corset is being worn. In all cases, the pressure of inflation of the bag 9 remains relatively low in order to avoid too strong a compression of the viscera. For example, the pressure of inflation of the abdominal bag is between 10 and 100 millibars and the pressure of inflation of the tubes varies from 1.5 to 2 bars.

FIGS. 1 and 3 show a corset which further comprises a chin support 10. This is supported by a rigid rod 11 threaded in one of the deformable sheaths arranged between the inflatable tubes so that the height of the chin support may easily be adjusted by moving the rod 11 in the sheath which contains it.

Similarly, FIGS. 2 and 3 show a nape support 12, whose height is adjustable, supported by a rod 13 threaded in a deformable sheath arranged between two inflatable tubes.

FIG. 2 shows two windows 14a and 14b cut out in the lumbar region of the vest, on either side of the structure 8, to enable the reduction of the lumbar lordosis to be verified.

FIGS. 4 and 5 show a variant embodiment in which the vest 2 is constituted by two separate parts, a front part 2a shown in FIG. 4 and a back 2b shown in FIG. 5. These two parts are assembled together, on each side, for example by tabs 16 of the touch and close type or by straps, or any other equivalent assembly means which enables the two parts to be separated and fitted closely to the body. This embodiment enables vest fronts and backs to be manufactured for each size, comprising inflatable structures of different length, and two halves to be matched of which the lengths of the structures are adapted to the malformation which is to be corrected. The other parts of the vest shown in FIGS. 4 and 5 are similar to those of FIGS. 1 to 3 and bear the same references. In particular, the front is provided, on the left-hand side, with a slide fastener 6 which allows the vest to be removed and replaced without modifying the adjustment of assembly means 16.

The broken lines 17a and 17b represent the shape of the upper edge of the front and rear of the vest in a variant embodiment not having shoulder straps 4a and 4b.

FIG. 6 is a horizontal section through VI—VI of FIGS. 1 or 4.

This Figure shows the fabric of the vest 2 on the outside of which is fixed the inflatable structure 7. The section of the rear structure 8 is identical to that of structure 7.

The inflatable structures 7 and 8 are composed of a plurality of inflatable tubes 18, for example six, which are enclosed in a fabric envelope 19 which is sewn at several points 20 on the vest 2.

The section of the tubes 18 may be circular or, preferably, as shown in FIG. 6, have two opposite side faces 18a and 18b which are flat.

The envelope 19 defines with the wall of the vest 2 elongated deformable sheaths 21 closed at their ends, in each of which a tube 18 is enclosed.

Between these sheaths which each contain a tube, are arranged secondary sheaths 22, open at at least one of their ends, into each of which is inserted a pin 15. All the tubes of a structure communicate with one another by a tube (not shown) so that they are all inflated to the same pressure via the same mouthpiece.

FIG. 6 further shows a horizontal section through the inflatable bag 9 and the fixation thereof.

The bag 9, provided with the mouthpiece 9a for its inflation, is enclosed in a fabric envelope 23. The surface of this envelope facing the vest comprises a double wall 23a, 23b containing a plate 24, for example a plate made of semi-rigid plastics material which constitutes a surface for distributing the forces between the bag 9 and the structure 7.

The width of the wall 23a of the envelope 23 at the side of the vest is determined by the width of the plate 24.

The wall 23c, placed against the abdomen, is wider than the wall 23a. The width of wall 23c determines the depth of penetration of the bag 9 inside the abdominal cavity. The bag 9 is removably fixed on the inside of the vest 2. For example, the wall 23b comprises fastening strips 25a and 26a of the touch and close type which cooperate with strips 25b and 26b fixed to the inside of the vest so that the bag 9 may be varied in height.

The volume and the position in height of the bag 9 as well as the width of the plate 24 and of wall 23c may vary according to the degree of malformation and the size of the patient.

FIG. 7 shows a section through a variant embodiment, along VI—VI.

This Figure shows the inflatable bag 9 placed in a fabric envelope 23 composed of three walls 23a, 23b and 23c and the plate 24 inserted between walls 23a and 23b as well as the touch and close fasteners 25a and 26b fixed to a wall 23b.

In this variant embodiment, the inflatable tubes 18 are circular in transverse section or have two flat side walls. They are placed inside an envelope 27 formed of two strips of fabric 27a and 27b which are sewn together by means of peripheral stitching 28 so that they constitute a closed envelope.

The inside of this envelope is divided into elongated compartments by transverse partitions 29 made of fabric which are fixed along their edges by stitches 30 to the two walls 27a and 27b. The sucessive compartments defined by these partitions and by the walls 27a and 27b are occupied alternately by a tube 18 and by a pin 15 so that, when the tubes 19 are inflated, each pin is gripped between two tubes and immobilised in the sheath which contains it. In this example, the envelope 27 is not sewn on the outside of the vest 2 but is fixed by peripheral stitching 31 to the edges 32 of an opening or vertical window cut out from the vest 2. The touch and close fasteners 25b and 26b are fixed on the wall 27b of the envelope.

We claim:

1. An orthopaedic corset for correcting the deformations of the spine, comprising:
   a vest made of non-stretch material which envelopes the trunk of the wearer;
   separate front and rear stiffening structures, each comprising a separate group of a plurality of vertical inflatable tubes, said stiffening structures each being fixed to said vest in predetermined positions, with said rear stiffening structure being located along the axis of the back of the wearer and the front stiffening structure being located in the center of the front of the wearer;
   and an inflatable bag secured to said vest and located thereon to be placed against the abdominal cavity under the front stiffening structure when the vest is worn, whereby predetermined forces are applied to the wearer to straighten the spine.

2. An orthopaedic corset for correcting the deformations of the spine, comprising a vest made of non-stretch material which envelopes the trunk of the wearer, separate front and rear stiffening structures, each comprising a separate group of a plurality of vertical inflatable tubes, said stiffening structures each being fixed to said vest in predetermined positions, with said rear stiffening structure being located along the axis of the back of the wearer and the front stiffening structure being located in the center of the front of the wearer; and an inflatable bag secured to said vest and located thereon to be placed against the abdominal cavity under the front stiffening structure when the vest is worn; said stiffening structures each comprising,
   vertical deformable sheaths arranged between said inflatable tubes;
   and rigid pins placed in certain of said sheaths.

3. The orthopaedic corset as claimed in claim 2, wherein said deformable sheaths are open at at least one of their two ends and said rigid pins are held in said sheaths by the grip of the tubes when the tubes are inflated; said rigid pins being removable from said sheaths when the tubes are inflated.

4. The orthopaedic corset as claimed in claim 1, wherein the front stiffening structure extends from the sternum to the lower edge of the vest, which lower edge is located approximately at the level of the pubis.

5. The orthopaedic corset as claimed in claim 1, wherein the rear stiffening structure extends from the shoulder blades to the lower edge of the vest which lower edge is located approximately at the level of the sacrum.

6. The orthopaedic corset as claimed in claim 3, including a chin support carried by at least one of said rigid rods, said rigid rods being respectively threaded in said deformable sheaths, which are open at their upper end.

7. The orthopaedic corset as claimed in claim 3, including a nape support carried by at least one of said rigid rods, said rigid rods being respectively threaded in deformable sheaths, which sheaths are open at their upper end.

8. The orthopaedic corset as claimed in claim 1, including a semi-rigid plate arranged between said inflatable bag and said front stiffening structure.

9. The orthopaedic corset as claimed in claim 8, wherein said inflatable bag is enclosed in a fabric envelope having an inner portion which comprises two walls having said semi-rigid plate inserted therebetween, and means for removably fixing said envelope to the inside of the vest at an adjustable height.

10. The orthopaedic corset as claimed in claim 1, including
    means for adjusting the vest to the body comprising deformable, expansible side elements, laces for adjustably connecting the front and rear edges of these expansible elements and adjustable tabs which pass over each shoulder and which connect the front and rear of the vest;
    and closure means constituted by a vertical slide fastener located on one side of the front of the vest.

11. The orthopaedic corset as claimed in claim 2, wherein said stiffening structures each comprise a fabric envelope which defines a first set of sheaths, in each of which is enclosed an inflatable tube and a secondary set of sheaths which are arranged between said first sheaths, and in each of which is inserted at least one rigid pin.

* * * * *